Feb. 27, 1951 F. H. HOWARD Plant Pat. 1,006
ROSE PLANT
Filed Feb. 6, 1950
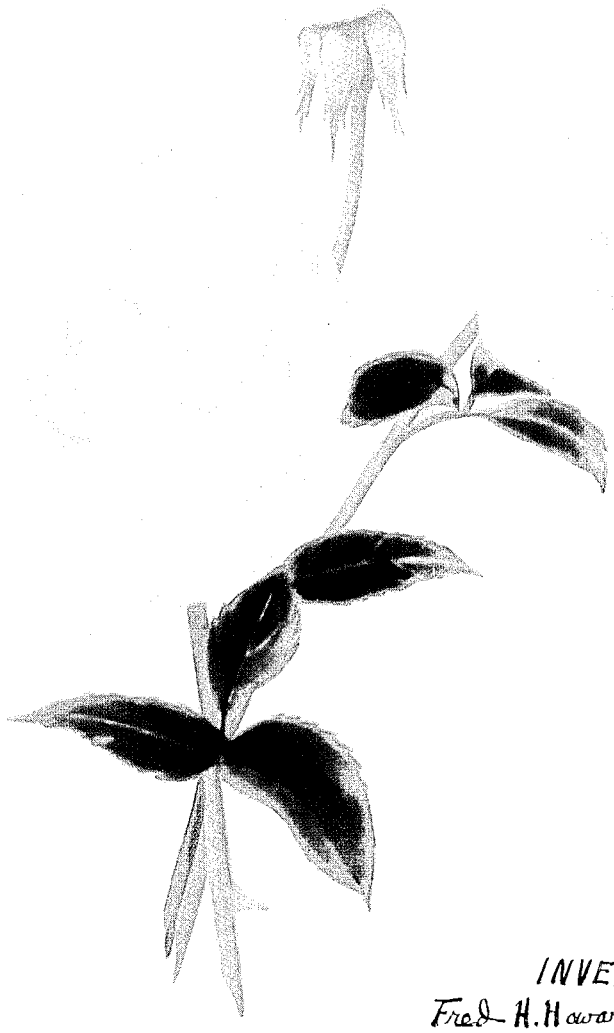
INVENTOR
Fred H. Howard, deceased
By Minnie J. Howard, Executrix
By Orville M. Kile
Plant Pat. Agt.

Patented Feb. 27, 1951

Plant Pat. 1,006

UNITED STATES PATENT OFFICE 1,006

ROSE PLANT

Fred H. Howard, deceased, late of Montebello, Calif., by Minnie J. Howard, executrix, Montebello, Calif., assignor to Howard & Smith, Montebello, Calif.

Application February 6, 1950, Serial No. 142,561

1 Claim. (Cl. 47—61)

The present invention pertains to a new variety of hybrid tea rose plant of strong growth habit, long blooming period and one that produces flowers predominantly golden yellow with pink shadings.

The variety is a cross between the variety Pearl Harbor (Plant Patent No. 637) and an unnamed seedling whose parentage is not known to me. It has been reproduced by budding in gardens at Montebello, California, and its characteristics appear to be permanent.

The accompanying illustrations show three typical specimens of the flower of this variety in various stages of opening, together with portions of the foliage and stems—all in approximately their true colors.

Following is a more detailed description of this new variety, in which color plate numbers refer to Ridgway's Color Standards and Nomenclature and other color references indicate the ordinary dictionary meaning of the term.

*The plant*

Type: Hybrid tea.

Growth habit: Upright bush. Very strong grower.

Blooming habit: Very floriferous, producing flowers continuously over a longer period than other roses of similar coloring.

Stems: Long, from 15 to 20 inches. Medium strength. Light green with red tinge.

Thorns: Average quantity, horizontal, sharp, red-tinged, approximately ⅜ inch long.

Foliage:

*Type.*—Pinnately compound, with 5 to 7 leaflets.

*Quantity.*—Average.

*Leaflets.*—Long oval with sharp apex. Terminal leaflet approximately 2 inches long by 1½ inches wide.

*Stipules.*—Long; very prominent.

*The flower*

Bud:

*Size.*—About 1½ inches long, opening wide to 4 inches.

*Form.*—Ovoid.

*Color.*—Light golden, tinted light red.

*Peduncle.*—Rigid; about 2 inches long.

*Sepals.*—Simple except they are branching at ends; medium length; reflex early; overlapping.

Bloom:

*Size.*—Opens to 4 inches in diameter.

*Form.*—Compressed; petals roll gently backward.

*Petals.*—Ovate to orbicular.

*Petalage.*—50 to 60 petals.

*Color.*—Golden orange, with pink shadings—particularly on the petal edges. The predominating color lies between Buff Yellow (Plate IV) and Deep Chrome (Plate III), and the pink shadings range from Safrano Pink (Plate II) to Eosine Pink (Plate I).

*Fragrance.*—Slight tea fragrance.

*Longevity.*—Keeping qualities as cut flower very good.

*Reproductive organs.*—*Stamens* many. *Anthers* golden yellow and prominent. *Filaments* red. *Styles* low and conical.

*Comparison*

The variety most like this new variety is Lolita Armour (unpatented), the similarity being principally in flower color. Chief differences are as follows:

1. This variety is a much stronger grower.
2. This variety has much longer stems.
3. This variety is much more floriferous, producing more flowers and over a longer period.
4. Although general colors of the flowers of the two varieties bear a resemblance, the orange in this flower is considerably more pronounced and the pink shadings are much stronger.

Having thus disclosed this invention, it is claimed:

The new and distinct variety of hybrid tea rose plant, substantially as herein shown and described, characterized by the combination of its very strong growth; prolific production of flowers over a long period; its long stems; its short peduncle; and its flowers which are golden yellow with pink shadings.

MINNIE J. HOWARD,
*Executrix of the Last Will and Testament of Fred H. Howard, Deceased.*

No references cited.